United States Patent
Biber et al.

(10) Patent No.: US 11,275,135 B2
(45) Date of Patent: Mar. 15, 2022

(54) METHOD AND DEVICE FOR TAKING ACCOUNT OF THE MAGNETIC RESONANCE SIGNAL DURING INTERFERENCE SUPPRESSION

(71) Applicant: Siemens Healthcare GmbH, Erlangen (DE)

(72) Inventors: Stephan Biber, Erlangen (DE); David Grodzki, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/938,901

(22) Filed: Jul. 24, 2020

(65) Prior Publication Data

US 2021/0025954 A1   Jan. 28, 2021

(30) Foreign Application Priority Data

Jul. 25, 2019   (EP) .................................... 19188305

(51) Int. Cl.
| | |
|---|---|
| *G01R 33/36* | (2006.01) |
| *A61B 5/055* | (2006.01) |
| *G01R 33/385* | (2006.01) |
| *G01R 33/54* | (2006.01) |
| *G01R 33/56* | (2006.01) |

(52) U.S. Cl.
CPC .......... *G01R 33/3621* (2013.01); *A61B 5/055* (2013.01); *G01R 33/385* (2013.01); *G01R 33/543* (2013.01); *G01R 33/5608* (2013.01)

(58) Field of Classification Search
CPC .......................... G01R 33/3621; G01R 33/385; G01R 33/543; G01R 33/5608; A61B 5/055
See application file for complete search history.

(56) References Cited

U.S. PATENT DOCUMENTS

| | | |
|---|---|---|
| 2004/0164739 A1 | 8/2004 | Peterson |
| 2008/0048658 A1 | 2/2008 | Hushek |
| 2017/0108569 A1* | 4/2017 | Harvey ................ G01R 33/422 |

FOREIGN PATENT DOCUMENTS

| | | |
|---|---|---|
| EP | 3467531 A1 | 4/2019 |
| JP | 2018201599 A | 12/2018 |

OTHER PUBLICATIONS

Bernstein, Matt A. et al. "Handbook of MRI Pulse Sequences", Elsevier, 2004; ISBN-13:978-0-12-092861-3, Chapter 13.2. pp. 1-52.
European Search Report for European Application No. 19188305.7-1010 dated Feb. 4, 2020.

* cited by examiner

*Primary Examiner* — Gregory H Curran
(74) *Attorney, Agent, or Firm* — Lempia Summerfield Katz LLC

(57) ABSTRACT

A method for suppressing interference signals during an image acquisition with a magnetic resonance tomography scanner that has an antenna and an interference signal sensor is provided. The magnetic resonance tomography scanner receives a reference interference signal via the interference signal sensor, receives a magnetic resonance signal via the antenna, and reduces a portion of an interference signal in the magnetic resonance signal as a function of the reference interference signal. During the reduction of the interference signal, the method takes into account the fact that the reference interference signal also has a signal portion of the magnetic resonance signal.

17 Claims, 2 Drawing Sheets

METHOD AND DEVICE FOR TAKING ACCOUNT OF THE MAGNETIC RESONANCE SIGNAL DURING INTERFERENCE SUPPRESSION

This application claims the benefit of European Patent Application No. EP 19188305.7, filed on Jul. 25, 2019, which is hereby incorporated by reference in its entirety.

BACKGROUND

The present embodiments relate to active interference suppression in a magnetic resonance tomography scanner and a magnetic resonance tomography scanner with a receiver.

Magnetic resonance tomography scanners are imaging devices that, in order to map an examination object, align nuclear spins of the examination object with a strong external magnetic field and use a magnetic alternating field to excite the nuclear spins for precession about this alignment. The precession or return of the spins from this excited state into a state with less energy generates, as a response, a magnetic alternating field that is received by antennae.

A spatial encoding scheme is impressed on the signals with the aid of magnetic gradient fields. The spatial encoding subsequently enables the received signal to be assigned to a volume element. The received signal is then evaluated, and a three-dimensional imaging representation of the examination object is provided. In order to receive the signal, local receiving antennae (e.g., local coils) that are arranged directly on the examination object in order to attain an improved signal-to-noise ratio may be used. The receiving antennae may also be installed in a patient couch.

Magnetic resonance tomography scanners use radio frequency shielding in two respects. On the one hand, radio frequency pulses with powers in the kilowatt range, which are absorbed only partially in the patient, are generated in order to excite the nuclear spins. Radio waves leaving the patient aperture are radiated into the room and are therefore to be shielded in order to comply with emission limits.

On the other hand, the magnetic resonance signals to be received for the imaging are extremely weak. In order to achieve a sufficient signal-to-noise ratio (SNR), external interference signals are to be.

For this reason, costly shielding cabins are installed around a magnetic resonance tomography scanner in the prior art in order to reduce both emissions and immissions.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an outlay for shielding is reduced.

The method is provided for suppressing interference signals during a magnetic resonance recording with a magnetic resonance tomography scanner. The suppression of interference signals may not merely be passive reduction by shielding measures but instead the implementation of acts and measures in the processing of the signals received. The magnetic resonance tomography scanner has a controller and a receiver. The receiver is configured to receive the magnetic resonance signals required for imaging from one or more antennae and to process these signals for a subsequent image reconstruction. This may include, for example, amplifying and filtering. The receiver is configured, for example, to process magnetic resonance signals at the Larmor frequency, where the Larmor frequency is predetermined by a static magnetic field B0 of the magnetic resonance tomography scanner and the magnetic moment or spin of the nuclei to be acquired.

The magnetic resonance signal is received by one or more antennae (e.g., a local coil with antenna coils or a body coil). The receiver may have individual receive channels for each antenna coil or also receive channels for combined signals of several antennae. The magnetic resonance signal of the antennae may be a signal that is generated at least predominantly by a resonance of excited nuclear spins of the nuclei to be examined. A portion of noise or other interference signals, which are, however, attenuated by 12 dB, 18 dB, 24 dB, 36 dB, or more with respect to the signal of the nuclear spins, is unavoidable.

The magnetic resonance tomography scanner further includes one or more interference signal sensors. An interference signal sensor may be an antenna or sensor that receives the interference signal more strongly than the magnetic resonance signal (e.g., by 6 dB, 12 dB, 18 dB, or more above the magnetic resonance signal). The interference signal sensor may be an antenna that, for example, on account of a position of the antenna outside of the patient tunnel, may receive the interference signal. In one embodiment, however, a dedicated sensor, such as an induction coil, that picks up an interference signal from a feed line may be provided.

In one act of the method according to the present embodiments, the receiver receives a reference interference signal via the interference signal sensor. In another act, the receiver receives the magnetic resonance signal via the antenna. The acquisition of the reference interference signal may take place at separate times (e.g., during disjoint time sections) from the acquisition of the MR signal so that the interference signal sensor may also be an antenna for image acquisition. Alternatively, there is a spatial separation on account of an interference signal sensor also being arranged spatially at a distance from the antenna for receiving the MR signal.

In one embodiment, the reference interference signal also has a small portion of the magnetic resonance signal, as already explained in relation to the interference signal sensor. Although it is possible for both signals to be received simultaneously, the two signals may be received at different times or alternately simultaneously and separately. For example, in the case of temporal separation, a magnetic resonance signal may be the received emission of the nuclear spins, even if this is not used further for imaging. On account of the exponential decay of the signals of the nuclear spins over time, magnetic resonance signals are present even outside the receive window used for imaging, albeit with a lower intensity.

In a further act, the receiver reduces a portion of the interference signal in the magnetic resonance signal as a function of the reference interference signal. For example, the receiver may use an amplifier to amplify the reference interference signal of the interference signal detector by a certain factor and delay the reference interference signal with a delay element in the phase such that the reference interference signal corresponds precisely in the amount of the amplitude to the portion of the interference signal in the magnetic resonance signal of the antenna and has an inverted sign. For example, by a summation element, the portion of the interference signal in the magnetic resonance signal may thus be reduced (e.g., almost to zero) by adding the two signals together. The receiver and/or the controller determine the attenuation of the interference signal in the magnetic resonance signal as well as the phase shift (e.g., through the autocorrelation of the magnetic resonance signal and the reference interference signal).

It is, however, always the case here that a small portion of the magnetic resonance signal will also be contained in the reference interference signal, at least if the determination of the attenuation and the phase shift of the interference signal in the magnetic resonance signal are determined or adjusted during an imaging procedure, since the decay of the magnetic resonance signal is exponential and thus at least theoretically never completely reaches zero. In the case of simple interference suppression, the portion of the magnetic resonance signal received by the interference signal sensor is incorrectly interpreted as an interference signal, subtracted from the magnetic resonance signal received via the antenna, and thus results in a deterioration or artifacts in the imaging.

The method according to the present embodiments therefore further provides the act of implementing the reduction of the interference signal as a function of a portion of the magnetic resonance signal in the reference interference signal received by the interference signal sensor (e.g., determining or estimating an influence of the magnetic resonance signal on the reference interference signal and taking account of this in the subsequent determination of the parameters, such as attenuation and/or phase shift, for interference suppression in the magnetic resonance signal). Various ways of achieving this are provided below.

The method according to the present embodiments makes it possible in this way to reduce or prevent artifacts resulting from interference suppression.

In one embodiment of the method, the method has the act of populating a k-space with scan data of an image acquisition by a magnetic resonance scan. This may take place, for example, with a classic image acquisition using gradient echo sequences, in which the k-space is sampled row by row.

In a further act, a magnetic resonance signal is determined from this k-space scan data for a respective time instant of the acquisition of the reference interference signal. Because the acquisition of the reference interference signal does not necessarily take place at the same time as an acquisition of a magnetic resonance signal, which then corresponds to a point in the k-space, the magnetic resonance signal is interpolated during the acquisition of the reference interference signal from the k-space data between the measurement points.

According to one embodiment of the method, a method that is also referred to as gridding is used for this purpose. Gridding is typically used to convert scan data from a spiral or radial sampling for a simplified Fourier transform into the image space to a virtual sampling in rows of a Cartesian grid of the k-space (see also Handbook of MRI Pulse Sequences; Bernstein, King, Zhou; Elsevier Academic Press, ISBN-13: 978-0-12-092861-3, Section 13.2). In one embodiment of the method, gridding is used to determine the MR signal at the time instant of acquisition of the reference interference signal. With the thus determined portion of the magnetic resonance signal in the reference interference signal received by the interference signal sensor, it is possible, for example, by establishing the difference or using an adaptive filter to determine a reference interference signal without a magnetic resonance portion. From this filtered reference interference signal, parameters for a suppression of the interference signal in the magnetic resonance signal (e.g., the amplification and/or phase shift) are then determined by the controller or the receiver. Because the interference signal and the magnetic resonance signal are determined separately by the method according to the present embodiments, the interference signal received by the interference signal sensor may, for example, be stripped of the portion of the magnetic resonance signal (e.g., using adaptive filters or by subtracting the determined magnetic resonance signal portion) before being combined with the magnetic resonance signal of the antennae for the purpose of interference suppression. In one embodiment, the interference suppression of the magnetic resonance signal received by the antenna itself (e.g., by adaptive filters) may be parameterized, such that during interference suppression, a magnetic resonance signal portion in the interference signal remains disregarded.

Artifacts may thus be reduced by an MR signal interpreted as an interference signal without the need to perform additional, time-consuming MR scans.

In one embodiment of the method, the method has the act of determining quantitative information about the examination object using an MR scan. Quantitative information of this kind may be taken, for example, from T1 and/or T2 maps that are determined as part of a fingerprinting process in preparation for an image acquisition.

In one act of the method according to the present embodiments, a portion of the magnetic resonance signal in the reference interference signal is determined from the quantitative information. In one embodiment, on the basis of the quantitative information determined, an MR signal of the examination object is simulated or synthesized using Bloch equations in order to subtract the magnetic resonance signal thus determined from the reference interference signal or to take account of this magnetic resonance signal when reducing the interference signal in the magnetic resonance signal.

A synthetic magnetic resonance signal obtained in advance from quantitative information also makes it possible to determine a portion of the magnetic resonance signal in the reference interference signal and to take account of the portion of the magnetic resonance signal during interference suppression in order to reduce artifacts resulting from interference suppression.

In one embodiment, the method has an act to determine a transfer function of the magnetic resonance signal from the examination object to the interference signal sensor. In one embodiment, a field strength of the magnetic resonance signal may be calculated at the location of the interference signal detector using the Maxwell field equations. In another embodiment, as previously described for an estimated MR signal at the location of the examination object, this may be detected in the signal of the interference signal sensor using autocorrelation, and a transfer function may thus be determined.

In one embodiment, a measurement of the signal at the interference signal sensor may be repeated multiple times under the same conditions (e.g., with the same excitation sequence and the same geometric arrangement). A statistical interference signal would then be eliminated, while a repeatedly identical magnetic resonance signal portion increases as a result of superimposition. The transfer function may be determined therefrom.

Once determined, a transfer function may then be assumed to be constant, especially for an image acquisition with the same examination object and the same arrangement. In the event of changes, the act for determining the transfer function may then be repeated.

The transfer function makes it possible, with the magnetic resonance signal determined, to predict a portion of the magnetic resonance signal in the signal of the interference signal sensor more accurately.

In one embodiment of the method, the magnetic resonance tomography scanner has a plurality of antennae for receiving the magnetic resonance signal. During the act of reducing a portion of the interference signal in the magnetic resonance signal of a first antenna by the receiver, this is carried out as a function of the reference interference signal and a magnetic resonance signal of a second antenna. For suppression as a function of the reference interference signal, reference is made to the preceding explanations. Use is also made of the signals of a second antenna and/or further antennae during suppression. Conclusions may be drawn regarding the interference signal by correlating the signals received by the antennae. For example, using different spatial arrangements of the antennae, the interference signal may in each case be shifted in the phase between the antennae, so that by correlating the signals of the antennae, a phase shift is determined; the different phase shift is applied accordingly to the signal of the interference signal sensor before the signal of the interference signal sensor is subtracted from the magnetic resonance signal of the respective antenna in order to reduce the interference signal.

In one embodiment of the method according to the present embodiments, the magnetic resonance tomography scanner has a field camera. A field camera may be a device that is configured to record the magnetic field (e.g., the gradient field that is variable over time) in an area around the examination object in order thus to detect, for example, deviations caused by eddy currents or by the examination object itself. The field camera records the temporal sequence of the gradient field during a magnetic resonance scan. The portion of the magnetic resonance signal in the reference interference signal is then determined by the controller or the receiver as a function of the temporal sequence of the gradient field recorded by the field camera. This may take place, for example, using gridding, as already explained, where the k-space positions of the measurements are corrected using the magnetic field recorded by the field camera. During a simulation of the magnetic resonance signals with the aid of quantitative information, the corrected magnetic field values according to the recording of the field camera are used, for example, for the Bloch equations.

The recording of the gradient fields with a field camera makes it possible to determine the portion of the magnetic resonance signal in the reference interference signal more accurately, thus facilitating better correction.

In one embodiment of the method according to the present embodiments, the magnetic resonance tomography scanner has a plurality of antennae for receiving the magnetic resonance signal. These may be, for example, a plurality of antenna coils of a local coil matrix, a plurality of separate local coils that are arranged at different positions, or one or a plurality of local coils and the body coil.

With regard to the reduction of a portion of the interference signal in the magnetic resonance signal of a first antenna by the receiver, reference is made to the preceding explanations. In the present embodiment, at least the magnetic resonance signal acquired by a second antenna is also used for interference suppression. Interference suppression may take place as a function of the reference interference signal and a magnetic resonance signal of the second antenna. For example, use is made of the first antenna and the second antenna being offset spatially in relation to one another (e.g., where the distance to the interference signal sensor is concerned). As a result, an interference signal acquired by the interference signal sensor is also shifted by a certain phase amount when the interference signal is received by the first antenna and the second antenna. The phase amount corresponds to a difference in distance divided by the propagation velocity. In the opposite direction, a magnetic resonance signal that was acquired by the first antenna and the second antenna, respectively, arrives with a corresponding phase delay. In this way, an approximate estimation of the magnetic resonance signal in the interference signal may, for example, be performed by a weighted total across the first antenna, the second antenna, and any further antennae with a different phase shift in each case in order then to subtract the estimation from the received signal of the interference signal sensor.

The inclusion of the signals of a second antenna or further antennae when reducing the interference signal in the magnetic resonance signal of the first antenna enables a more accurate estimation and thus fewer image artifacts.

DETAILED DESCRIPTION

Figure 1:
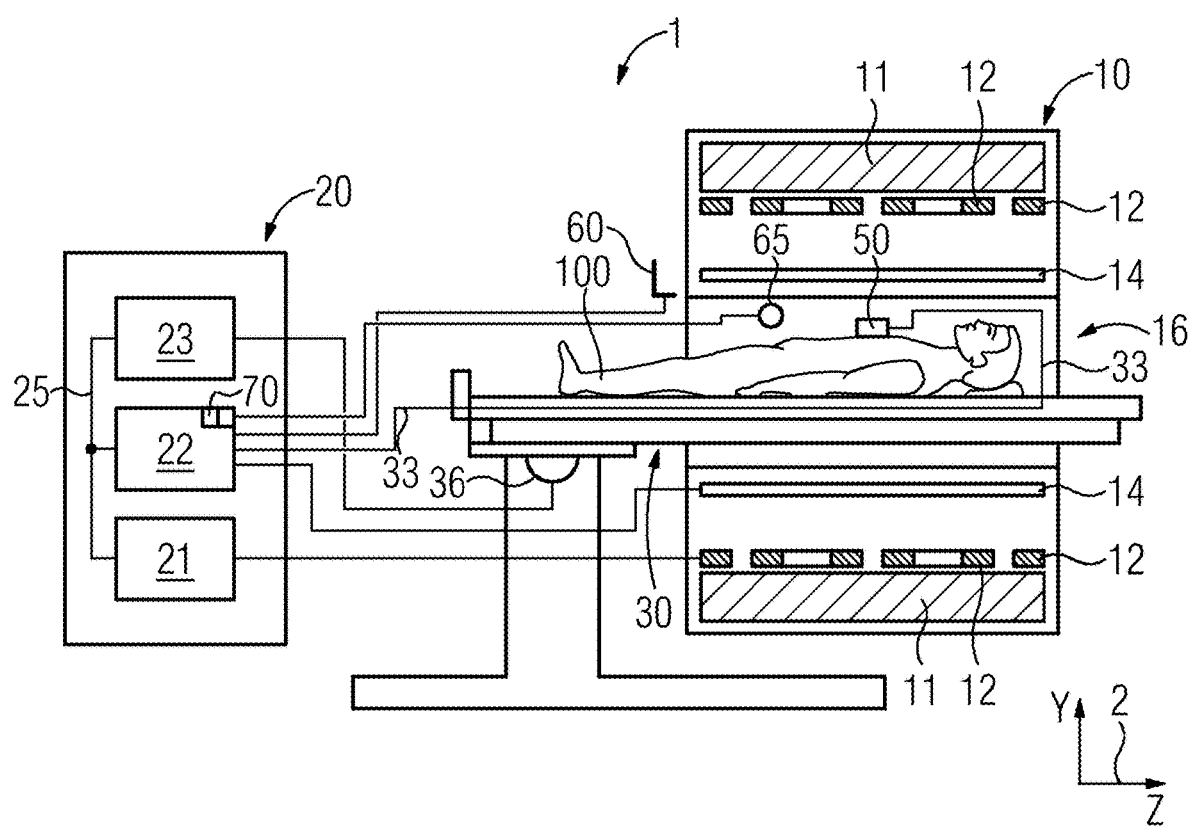
FIG. 1 shows a schematic representation of a magnetic resonance tomography scanner for carrying out a method according to an embodiment.

FIG. 1 shows a schematic representation of a magnetic resonance tomography scanner 1 having one embodiment of a local coil 50.

The magnet unit 10 has a field magnet 11 that generates a static magnetic field B0 for aligning nuclear spins of samples or of the patient 100 in an acquisition zone. The acquisition zone is characterized by an extremely homogeneous static magnetic field B0; the homogeneity relates, for example, to the magnetic field strength or an absolute value of the magnetic field strength. The acquisition zone is virtually spherical in shape and is arranged in a patient tunnel 16 that extends in a longitudinal direction 2 through the magnet unit 10. A patient couch 30 is movable in the patient tunnel 16 by the positioning unit 36. Typically, the field magnet 11 is a superconducting magnet that is able to provide magnetic fields having a magnetic flux density of up to 3 T or even more in more recent devices. For lower field strengths, however, permanent magnets or electromagnets having normally conducting coils may also be used.

In addition, the magnet unit 10 has gradient coils 12 that are configured to overlay the magnetic field B0 with variable magnetic fields in three spatial directions for the purpose of spatially differentiating the acquired mapping regions in the examination volume. The gradient coils 12 are typically coils made from normally conductive wires that may generate fields orthogonal to one another in the examination volume.

The magnet unit 10 also includes a body coil 14 that is configured to radiate a radio frequency signal supplied by a signal line into the examination volume and to receive resonance signals emitted by the patient 100 and output the signals via a signal line.

A control unit 20 (e.g., a controller) supplies the magnet unit 10 with the different signals for the gradient coils 12 and the body coil 14 and evaluates the received signals.

Accordingly, the control unit 20 has a gradient controller 21 that is configured to supply the gradient coils 12 via supply lines with variable currents that provide the desired gradient fields in the examination volume in a time-coordinated manner.

In addition, the control unit 20 has a radio frequency unit 22 that is configured to generate a radio frequency pulse having a predefined temporal sequence, amplitude, and spectral power distribution for exciting a magnetic resonance of the nuclear spins in the patient 100. Pulse powers in the kilowatt range may be achieved in this case. The excitation pulses may be radiated into the patient 100 by the body coil 14 or also by a local transmit antenna.

A controller 23 communicates with the gradient controller 21 and the radio frequency unit 22 via a signal bus 25.

A local coil 50 is arranged as a first antenna on the patient 100 and is connected to the radio frequency unit 22 and a receiver of the radio frequency unit 22 via a connecting lead 33. The body coil 14 may, however, be a first antenna within the present embodiments.

Four interference signal sensors 60 are arranged (e.g., at the corners of a square inscribed within the circular opening) at an edge of the opening of the patient tunnel 16 so that the corners come to rest on the edge of the opening. The four interference signal sensors 60 have a signal connection with the receiver 70 of the radio frequency unit 22. On account of the plurality of interference signal sensors 60, not all of the plurality of interference signal sensors 60 may have an omnidirectional receive characteristic; instead, the plurality of interference signal sensors 60 may, for example, be dipoles and may supplement one another on account of the different alignment to form an omnidirectional characteristic. In one embodiment, a crossed-dipole antenna is provided as a single second antenna with an omnidirectional characteristic.

In one embodiment, an interference signal sensor 60 may be arranged alternatively or in addition in the patient couch 30.

The patient tunnel may have, for example, a radius R, for which the following applies:

$$R < (\text{Lambda}_L * 1.841)/(2 * \text{Pi})$$

Here, $\text{Lambda}_L$ specifies the wavelength of a radio wave in air at the Larmor frequency of the magnetic resonance tomography scanner 1. If the radius R is smaller than the right term, the radio wave is propagated with exponential attenuation in the patient tunnel 16, and the interference signal is strongly attenuated in the center in the examination region FoV. $\text{Lambda}_L$ is also referred to as the cut-off wavelength of a circular hollow waveguide, and the associated frequency is also referred to as the cut-off frequency.

Only the patient 100 acts, on account of his finite conductivity, as the core of a coaxial cable, the sheath of which is the wall of the patient tunnel 16, and conducts an electromagnetic signal coupled in at the legs or head end into the examination region. The interference signal sensor 60 or the interference signal sensors 60 in the vicinity of the aperture or in the patient couch 30, for example, receive the interference signal conducted into the FoV by the patient 100, thus rendering the compensation in the receiver 70 particularly effective.

However, the patient 100 also conducts a magnetic resonance signal in the opposite direction out of the patient tunnel 16 to the interference signal sensor or sensors 60. If this is received by the interference signal sensor 60 and handled as an external interference signal (e.g., subtracted in the magnetic resonance signal received by the local coil 50 and/or body coil 14), then this results in falsifications of the magnetic resonance signal and, on account of the association with the imaging magnetic resonance signal, to image artifacts.

The controller 23 and/or the receiver 70 of the magnetic resonance tomography scanner according to the present embodiments are therefore configured to carry out the reduction of the interference signal as a function of a portion of the magnetic resonance signal in the reference interference signal received by the interference signal sensor 60.

Figure 2:
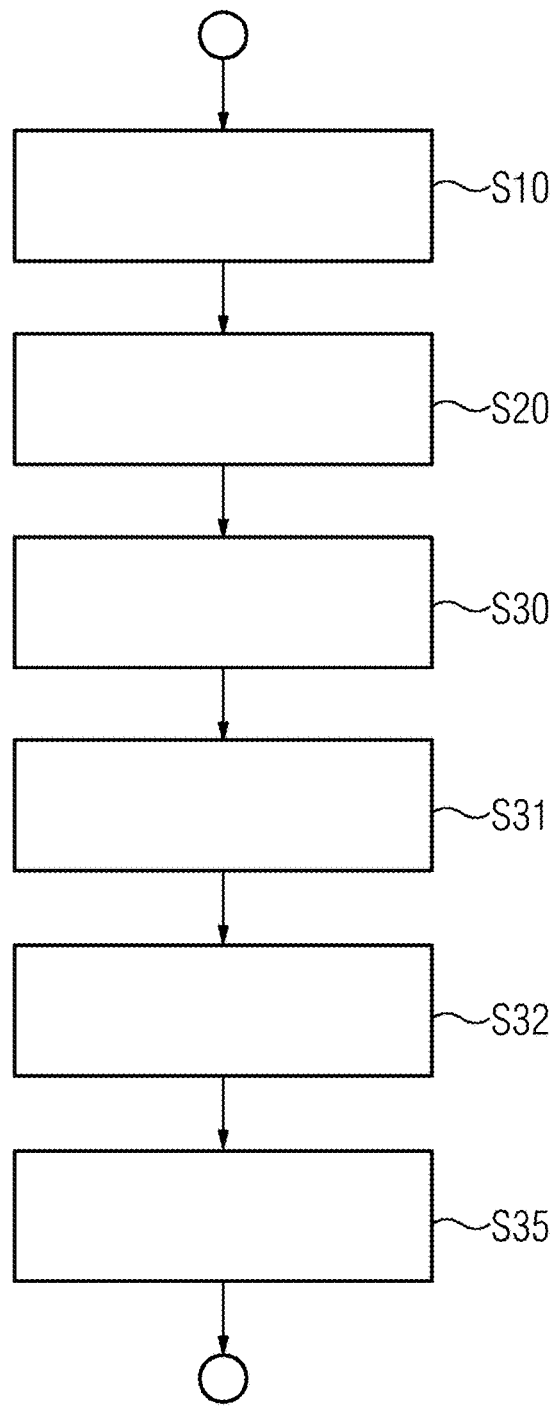
FIG. 2 shows a schematic representation of an exemplary flow diagram of one embodiment of the method.

The receiver 70 and/or the controller 23 carry out the method according to the present embodiments shown in FIG. 2. In one embodiment, the method may be carried out in a program-controlled manner by a processor (e.g., a signal processor). Alternatively, the present embodiments may be realized by a logic in an FPGA or ASIC.

In act S10 of the method according to one or more of the present embodiments, the receiver 70 receives a reference interference signal via the interference signal sensor 60. The reference interference signal also has a portion of a magnetic resonance signal that is radiated from the patient 100, even if no magnetic resonance signal is simultaneously received via the local coil 50 or the body coil, since the magnetic resonance signal remains present in attenuated form for a longer time on account of exponential decay of the magnetic resonance signal.

In act S20, the magnetic resonance tomography scanner 1 receives a magnetic resonance signal from the patient 100 with the receiver 70 via an antenna (e.g., the local coil 50) that may also be configured with several antenna coils as a local coil matrix, or the body coil 14. The act S10 and the act S20 do not necessarily take place simultaneously, but may also take place consecutively. Following processing according to the method according to the present embodiments, the received magnetic resonance signal is used further for imaging by the controller 23 or a separate unit for image reconstruction, and is finally output on a screen, for example.

In act S30, the receiver 70 reduces a portion of the interference signal in the magnetic resonance signal as a function of the reference interference signal. This may take place, for example, by the signal received by the interference signal sensor 60 being added to the signal of the local coil 50 with a predetermined weighting and phase shift, so that precisely the portions of the interference signal in the signal of the local coil 50 are canceled with the weighted signal. The phase shift and weighting may be determined, for example, through autocorrelation of the signals of the interference signal and the signal of the local coil 50.

However, the method according to the present embodiments is characterized, for example, in that, in act S30, the method also takes into account that the signal of the interference signal sensor 60 always also contains a portion of a magnetic resonance signal, at least during an image acquisition with a patient 100. For this reason, the method according to the present embodiments provides that the act S30 is carried out as a function of a portion of the magnetic resonance signal in the reference interference signal received by the interference signal sensor 60.

This may be achieved by, in one embodiment of the method, a k-space being populated with scan data of an image acquisition, such as, for example, a gradient echo sequence, by a magnetic resonance scan S31. The magnetic resonance scan may take place as part of a sequence or as a preparatory scan. In the simplest case, this may be a Cartesian grid in the k-space, the nodes of which are populated row by row and column by column with MR signals resulting from suitable sequences. Other sampling models along radial or spiral trajectories may, however, also be provided.

In act S32, the MR signal may be interpolated at any time instant through interpolation to these k-space points. Corresponding methods have been developed in order to determine the scan values for a Cartesian coordinate system for a spiral trajectory (e.g., "gridding"), for example, and then use a simpler inverse transformation into the image space. Methods of this kind are described, for example, in the "Handbook of MRI Pulse Sequences", Bernstein, King, Zhou; Elsevier Academic Press, ISBN-13:978-0-12-092861-3, Section 13.2. In this way, a magnetic resonance signal emitted from the patient 100 may be determined at least approximately, while in act S10, the reference interference signal is recorded with the interference signal sensor 60.

Figure 3:
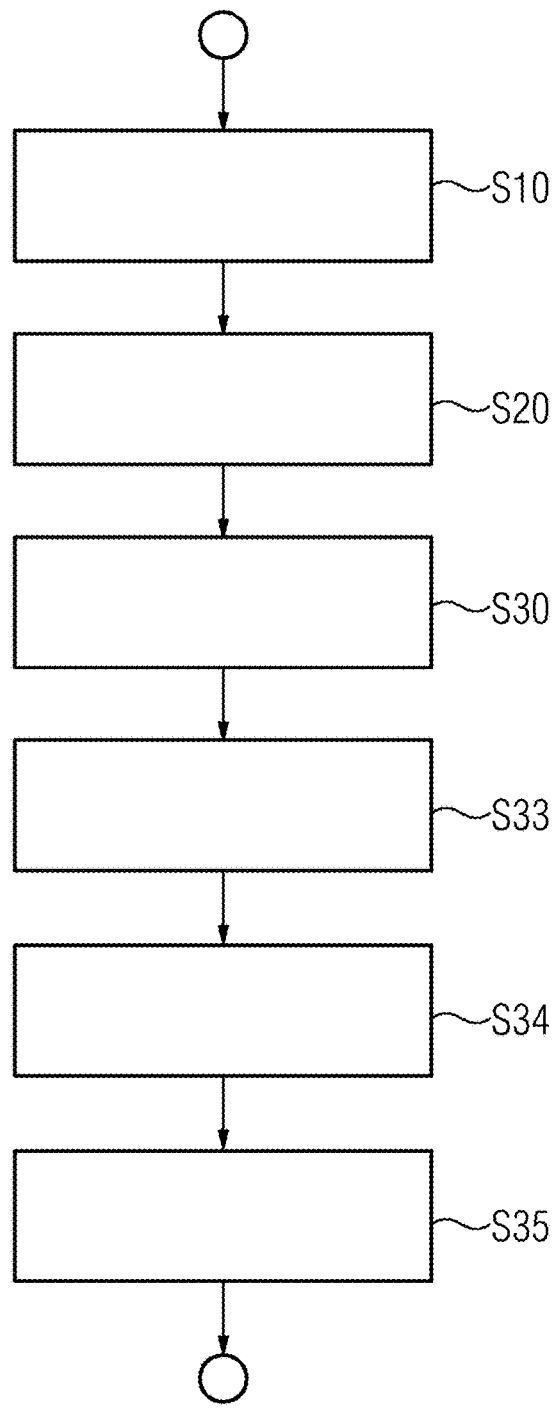
FIG. 3 shows a schematic representation of an exemplary flow diagram of another embodiment of the method.

In another exemplary embodiment shown in FIG. 3, quantitative information about the examination object may be acquired with a magnetic resonance scan S33. This may be, for example, a spin density of the nuclear spins per volume element. From this quantitative information, a portion of the magnetic resonance signal in the reference interference signal received in act S10 is determined in act S33. In act S34, a size of the portion of the magnetic resonance signal received during act S10, for example, may be determined using the quantitative information by a Bloch simulation from the spin density and a transfer function subsequently applied thereto.

Such a transfer function may be determined in act S35. In one embodiment, the transfer function may be simulated by Maxwell field equations if the receive characteristics of the interference signal sensor 60, an arrangement of the interference signal sensor 60 relative to the examination object, and the characteristics of the examination object are known.

In one embodiment, the transfer function may be determined by measurement in act S35. In the case of a known magnetic resonance signal at the location of the examination object, the magnetic resonance signal may be detected by the receiver 70 using autocorrelation in the receive signal of the interference signal sensor 60, and, in this way, the transfer function with key parameters (e.g., attenuation and phase shift) may be determined.

In one embodiment, a measurement of the signal of the interference signal sensor 60 may be repeated with the same excitation of the spins (e.g., identical sequences), and these may be added together or averaged. While a statistical interference signal is eliminated with an increasing number of repetitions as a result of the averaging, the strength of the magnetic resonance signal increases relative thereto, so that the transfer function for the magnetic resonance signal may be determined with sufficient accuracy if the averaging continues for long enough.

The act S35 may also have a combination of the described methods, so that, for example, even periodic interference signals do not disturb the method.

The act S35 may also be carried out at different time instants. The transfer function may be determined, for example, once for a type of a magnetic resonance tomography scanner 1. In one embodiment, the transfer function may be redetermined or adapted before one or each image acquisition or also between individual sequences, so that, for example, changes caused by movements of the patient 100 as the examination object may also be taken into account.

From the magnetic resonance signal determined and from the transfer function, a portion of the magnetic resonance signal to be expected in each case in the signal of the interference signal sensor 60 may then be determined at any time instant. If the portion thus determined is then added to the signal of the interference signal sensor, for example, with an inverted sign (e.g., with a phase shift of 180 degrees), then the magnetic resonance signal portion may be canceled, and a pure interference signal is obtained. In one embodiment, the magnetic resonance signal portion determined may be taken into account or suppressed by corresponding filter measures in the receiver 70 in the subsequent signal path in the analog or digital signal processing. This may be achieved, for example, using adaptive filters.

The magnetic resonance signal may deviate from an ideal magnetic resonance signal on account of undesirable side-effects, such as variations in the gradient fields caused by eddy currents. In one embodiment, the magnetic resonance tomography scanner 1 has a field camera 65, with which the magnetic field including the static portion B0 and the gradient fields is measured (e.g., during act S10 and/or act S20). A field camera 65 may, for example, have several samples with a material sensitive for nuclear spin excitation distributed over the patient tunnel, the magnetic resonance signal of which is acquired and thus permits an accurate determination of the magnetic fields at the location of the field samples. The field strength between the samples may also be determined therefrom by interpolation. In one embodiment, the magnetic field may be determined by magnetic field sensors such as Hall sensors. With the field strength determined, the Bloch simulation of the magnetic resonance signals in the receiver 70 or the controller 23 may, for example, be performed more accurately, and in this way, the portion of the magnetic resonance signal in the signal of the interference signal sensor 60 may be suppressed more effectively.

In one embodiment of the method, the magnetic resonance tomography scanner has a plurality of antennae for receiving the magnetic resonance signal. The plurality of antennae (e.g., local coils 50 or antenna coils of a local coil matrix) makes it possible, on account of the different positions relative to one another and to the patient 100 or the examination object, to evaluate different combinations of the same interference signal with a magnetic resonance signal, so that the interference signal may be differentiated in the signals of the antennae and filtered out more effectively; conversely, in the other direction, the magnetic resonance signal portion in the signal of the interference signal sensor may be detected and filtered. In the case of adjacent antennae of a local coil matrix, for example, the interference signal is approximately the same on account of the small distance between the adjacent antennae in comparison to the interference signal source outside of the patient tunnel 16, while the magnetic resonance signals for different volumes of the patient 100 may be differentiated. As a result, during simulation of the magnetic resonance portion, the magnetic resonance portion may then be modeled more accurately for the different locations of origin and then suppressed or compensated more effectively.

Although the invention has been illustrated and described in greater detail with the exemplary embodiments, the invention is not restricted by the examples disclosed, and other variations may be derived therefrom by the person skilled in the art without departing from the protective scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for suppressing interference signals in a magnetic resonance recording with a magnetic resonance tomography scanner, wherein the magnetic resonance tomography scanner includes a controller, a receiver, an antenna, and an interference signal sensor, the method comprising:
   receiving a reference interference signal by the receiver via the interference signal sensor;
   receiving a magnetic resonance signal of an examination object by the receiver via the antenna;
   determining an influence of the magnetic resonance signal on the reference interference signal received by the interference signal sensor; and
   reducing a portion of an interference signal in the magnetic resonance signal by the receiver as a function of the reference interference signal,
   wherein the reducing of the portion of the interference signal takes place as a function of the influence of the magnetic resonance signal on the reference interference signal received by the interference signal sensor.

2. The method of claim 1, further comprising:
   populating a k-space with scan data of an image acquisition by a magnetic resonance scan; and
   interpolating a portion of the magnetic resonance signal in the reference interference signal onto the scan data in the k-space with the aid of gridding.

3. The method of in claim 1, further comprising:
   determining quantitative information about the examination object by a magnetic resonance scan; and
   determining a portion of the magnetic resonance signal in the reference interference signal, the determining of the portion of the magnetic resonance signal in the reference interference signal comprising simulating the magnetic resonance signal with the quantitative information.

4. The method of claim 2, further comprising determining a transfer function of the magnetic resonance signal from the examination object to the interference signal sensor.

5. The method of claim 3, further comprising determining a transfer function of the magnetic resonance signal from the examination object to the interference signal sensor.

6. The method of claim 2, wherein the magnetic resonance tomography scanner further includes a field camera,
   wherein the method further comprises recording a temporal sequence of a gradient field by the field camera while receiving the magnetic resonance signal, and
   wherein the portion of the magnetic resonance signal in the reference interference signal is determined as a function of the temporal sequence of the gradient field recorded by the field camera.

7. The method of claim 3, wherein the magnetic resonance tomography scanner further includes a field camera,
   wherein the method further comprises recording a temporal sequence of a gradient field by the field camera while receiving the magnetic resonance signal, and
   wherein the portion of the magnetic resonance signal in the reference interference signal is determined as a function of the temporal sequence of the gradient field recorded by the field camera.

8. The method of claim 4, wherein the magnetic resonance tomography scanner further includes a field camera,
   wherein the method further comprises recording a temporal sequence of a gradient field by the field camera while receiving the magnetic resonance signal, and
   wherein the portion of the magnetic resonance signal in the reference interference signal is determined as a function of the temporal sequence of the gradient field recorded by the field camera.

9. The method of claim 1, wherein the magnetic resonance tomography scanner further includes a plurality of antennae for receiving the magnetic resonance signal, the plurality of antennae including the antenna, and
   wherein the reducing of the portion of the interference signal in the magnetic resonance signal comprises reducing the portion of the interference signal in the magnetic resonance signal of a first antenna of the plurality of antennae by the receiver as a function of the reference interference signal and a magnetic resonance signal of a second antenna of the plurality of antennae.

10. The method of claim 4, wherein the magnetic resonance tomography scanner further includes a plurality of antennae for receiving the magnetic resonance signal, the plurality of antennae including the antenna, and
    wherein the reducing of the portion of the interference signal in the magnetic resonance signal comprises reducing the portion of the interference signal in the magnetic resonance signal of a first antenna of the plurality of antennae by the receiver as a function of the reference interference signal and a magnetic resonance signal of a second antenna of the plurality of antennae.

11. A magnetic resonance tomography scanner comprising:
    a controller;
    a receiver;
    an antenna; and
    an interference signal sensor,
    wherein the magnetic resonance tomography scanner is configured to:
      receive a reference interference signal by the receiver via the interference signal sensor;
      receive a magnetic resonance signal of an examination object by the receiver via the antenna;
      determine an influence of the magnetic resonance signal on the reference interference signal received by the interference signal sensor; and
      reduce a portion of an interference signal in the magnetic resonance signal as a function of the reference interference signal by the receiver,
    wherein the reduction of the interference signal takes place as a function of a portion of the influence of magnetic resonance signal on the reference interference signal received by the interference signal sensor.

12. In a non-transitory computer-readable storage medium that stores instructions executable by a controller of a magnetic resonance tomography scanner to suppress interference signals in a magnetic resonance recording with a magnetic resonance tomography scanner, wherein the magnetic resonance tomography scanner includes a controller, a receiver, an antenna, and an interference signal sensor, the instructions comprising:

receiving a reference interference signal by the receiver via the interference signal sensor;

receiving a magnetic resonance signal of an examination object by the receiver via the antenna;

determining an influence of the magnetic resonance signal on the reference interference signal received by the interference signal sensor; and reducing a portion of an interference signal in the magnetic resonance signal by the receiver as a function of the reference interference signal, wherein the reducing of the portion of the interference signal takes place as a function of the influence of the magnetic resonance signal on the reference interference signal received by the interference signal sensor.

13. The non-transitory computer-readable storage medium of claim 12, wherein the instructions further comprise:

populating a k-space with scan data of an image acquisition by a magnetic resonance scan; and interpolating a portion of the magnetic resonance signal in the reference interference signal onto the scan data in the k-space with the aid of gridding.

14. The non-transitory computer-readable storage medium of claim 12, wherein the instructions further comprise:

determining quantitative information about the examination object by a magnetic resonance scan; and determining a portion of the magnetic resonance signal in the reference interference signal, the determining of the portion of the magnetic resonance signal in the reference interference signal comprising simulating the magnetic resonance signal with the quantitative information.

15. The non-transitory computer-readable storage medium of claim 13, wherein the instructions further comprise determining a transfer function of the magnetic resonance signal from the examination object to the interference signal sensor.

16. The non-transitory computer-readable storage medium of claim 13, wherein the magnetic resonance tomography scanner further includes a field camera, wherein the instructions further comprise recording a temporal sequence of a gradient field by the field camera while receiving the magnetic resonance signal, and wherein the portion of the magnetic resonance signal in the reference interference signal is determined as a function of the temporal sequence of the gradient field recorded by the field camera.

17. The non-transitory computer-readable storage medium of claim 12, wherein the magnetic resonance tomography scanner further includes a plurality of antennae for receiving the magnetic resonance signal, the plurality of antennae including the antenna, and wherein the reducing of the portion of the interference signal in the magnetic resonance signal comprises reducing the portion of the interference signal in the magnetic resonance signal of a first antenna of the plurality of antennae by the receiver as a function of the reference interference signal and a magnetic resonance signal of a second antenna of the plurality of antennae.

* * * * *